United States Patent [19]
Murray

[11] Patent Number: 5,797,680
[45] Date of Patent: Aug. 25, 1998

[54] MANUAL BONE CEMENT MIXING SYSTEM WITH VACUUM PUMP START-STOP DEVICE

[76] Inventor: William M. Murray, 2650 Spring Hill La., Enola, Pa. 17025

[21] Appl. No.: 707,648

[22] Filed: Sep. 5, 1996

[51] Int. Cl.⁶ .................................................. B01F 13/06
[52] U.S. Cl. .................................................. 366/139
[58] Field of Search .................................. 366/129, 130, 366/139, 189, 197, 241, 242, 244–247, 349, 601; 206/219, 221

[56] References Cited

U.S. PATENT DOCUMENTS

| | | |
|---|---|---|
| 795,082 | 7/1905 | Warner . |
| 2,184,225 | 12/1939 | Moduffee et al. . |
| 2,203,135 | 6/1940 | Farrington . |
| 2,453,914 | 11/1948 | Hollenback . |
| 2,696,022 | 12/1954 | Steinbock et al. . |
| 3,131,912 | 5/1964 | Steinbock . |
| 3,358,971 | 12/1967 | Steinbock . |
| 3,640,510 | 2/1972 | Lea . |
| 4,185,072 | 1/1980 | Puderbaugh et al. . |
| 4,277,184 | 7/1981 | Solomon . |
| 4,721,390 | 1/1988 | Lidgren ................................. 366/139 |
| 4,758,096 | 7/1988 | Gunnarsson ......................... 366/139 |
| 4,787,751 | 11/1988 | Bakels ................................... 366/110 |
| 4,854,716 | 8/1989 | Ziemann et al. ..................... 366/139 |
| 4,871,261 | 10/1989 | Randklev ............................. 366/139 |
| 4,961,647 | 10/1990 | Coutts et al. ........................ 366/139 |
| 4,973,168 | 11/1990 | Chan . |
| 5,015,101 | 5/1991 | Draenert ............................... 366/349 |
| 5,044,761 | 9/1991 | Yuhki et al. ......................... 366/139 |
| 5,100,241 | 3/1992 | Chan ..................................... 366/139 |
| 5,114,240 | 5/1992 | Kindt-Larsen ...................... 366/129 |
| 5,145,250 | 9/1992 | Planck et al. ........................ 366/8 |
| 5,193,907 | 3/1993 | Faccioli et al. ..................... 366/130 |
| 5,252,301 | 10/1993 | Nilson et al. . |
| 5,257,862 | 11/1993 | Gardner ............................... 366/139 |
| 5,265,956 | 11/1993 | Nelson et al. ....................... 366/139 |
| 5,328,262 | 7/1994 | Lidgren ................................ 366/139 |
| 5,348,391 | 9/1994 | Murray ................................. 366/139 |
| 5,368,386 | 11/1994 | Murray ................................. 366/139 |
| 5,395,167 | 3/1995 | Murray ................................. 366/139 |

FOREIGN PATENT DOCUMENTS

| | | |
|---|---|---|
| 558762 | 6/1958 | Canada . |
| 4535517 | 11/1970 | Japan ................................... 366/139 |
| 5388259 | 8/1973 | Japan . |
| 9310892 | 6/1993 | WIPO . |

OTHER PUBLICATIONS

Zimmer, Osteobond Vacuum Mixing System, Jun. 1993.
Stryker High Vacuum Cement Injection System, "Third Generation Cementing Technique", Jan. 1992.
Howmedica, The Simplex Enhancement Mixer, "The Howmedica Experience" Dec. 1985.
Depuy, Inc. Flyer "Prism Vacuum Mixing Bowl" (Received by Applicant Apr. 20, 1994).
FDA Database Printout Indicating 510K Approval of "Prism Bone Cement Mixing System", on Jan. 5, 1994 (Received by Applicant on May 24, 1994).
Depuy Prosource "Prism II Cartridge Mixing System" (Received by Applicant Aug. 1995).

*Primary Examiner*—Charles E. Cooley
*Attorney, Agent, or Firm*—Thomas Hooker, P.C.

[57] ABSTRACT

A system for mixing bone cement is disclosed. Dry PMMA powder and MMA liquid are mixed in a vacuum chamber. Gas from the mixture is vacuum drawn from the mixer by a vacuum source through a vacuum tube which extends between the mixer and the vacuum source. The vacuum source is actuated by creating a positive pressure pulse in the vacuum tube. The pressure pulse may be caused by closing the lid of the mixer, by squeezing an in-line pressure bulb in the vacuum tube or by squeezing a pressure bulb joined to the vacuum tube. The vacuum source is automatically deactivated when a positive vacuum pulse is detected. The second pressure pulse is caused when the vacuum tube is disconnected from the vacuum chamber.

13 Claims, 2 Drawing Sheets

MANUAL BONE CEMENT MIXING SYSTEM WITH VACUUM PUMP START-STOP DEVICE

FIELD OF THE INVENTION

The invention relates to a bone cement mixing system.

DESCRIPTION OF THE PRIOR ART

Bone cement is prepared by mixing a very fine cement powder, typically polymethylmethacrylate (PMMA), with a liquid monomer, typically methylmethacrylate (MMA). The cement is used as a grout for implanting prosthetic devices in live bone. Because the cement hardens quickly it is mixed in the operating room and is then transferred directly to a prepared implantation site. The mixing of PMMA and MMA is performed in a housing under sterile conditions. During mixing, gas voids or bubbles are trapped in the viscous cement. These voids form hollow inclusions in the cured cement which weaken the cement and increase the possibility of cement fracture and resultant loosening of an implanted prosthetic device.

Conventional in-bowl and in-syringe bone cement mixing devices have a vacuum mixing chamber, a lid which covers the chamber and seals the PMMA and MMA in the mixing chamber, and a rotary mixer which extends through the lid and into the mixing chamber. The mixer is manually rotated to mix the powder and liquid together and form bone cement. It is common practice to connect the mixing device to a vacuum source to reduce the internal pressure in the mixing device in an attempt to remove bubble gas from the cement during mixing.

Bone cement is mixed by placing fine PMMA powder and MMA liquid in a mixing chamber, either the bowl of an in-bowl mixer or the barrel of a syringe cartridge which is in turn placed in a housing. The mixing device is closed with a mixer extending into the cement powder and liquid and the device is connected to a vacuum source. The mixer is manually operated for a measured time interval to mix the powder and liquid and form the bone cement.

When the mixing device is closed, the vacuum source very rapidly reduces the pressure within the closed mixing chamber and rapidly draws the relatively large volume of air between the very fine dry particles of powdered PMMA out of the mixing chamber holding the PMMA. This occurs before the powder is fully wetted by the MMA and captured in a liquid or partially liquid body of cement.

Conventional in-bowl and in-syringe mixing devices require the operator to lose valuable time searching for the on switch, typically a foot pedal, to start the vacuum pump.

U.S. Pat. No. 5,395,167 discloses a bone cement mixing system including a vacuum pump which is automatically stopped after the cement is mixed. Automatic stopping of the pump occurs when a positive pressure increase is detected. A positive pressure increase is caused by the removal of the vacuum hose from the mixing chamber.

SUMMARY OF THE INVENTION

The invention is a bone cement mixing system which automatically turns the vacuum pump on when the cement is ready to be mixed without the need for an operator who is working in a sterile field to locate and actuate an on switch which is outside the sterile field.

The system includes a vacuum pump, an automatic start control and an automatic shutdown control. The shut down control is taught in U.S. Pat. No. 5,395,167. Automatic starting and stopping of the pump allows saving of valuable time in the operating room, and avoids the need for the operator to manipulate controls outside the sterile field, or to have the services of an assistant to do this.

Bone cement is mixed by placing the proper amounts of PMMA and MMA in a mixing chamber in body of the mixing device. In a first embodiment of the invention, the on switch is actuated by placing a lid on the body and then moving the lid toward the body. The lid acts as a piston to increase the pressure inside the mixing device. This positive pressure increase is detected by a sensor in the automatic vacuum source which turns the vacuum pump on.

In a second embodiment of the invention, a pressure bulb is provided in the vacuum line extending between the mixing device and the vacuum source. The bulb is squeezed after the PMMA and MMA have been placed in the mixer and the lid has been placed on the body. Squeezing of the bulb creates a pressure pulse which is sensed to actuate the vacuum pump.

In a third embodiment of the invention, a pressure bulb is connected to a branch of the vacuum line. This bulb also generates a pressure pulse which actuates the vacuum pump.

In all three embodiments, a pressure pulse actuates a sensor to turn a vacuum pump on. The vacuum pump then withdraws air from the closed mixing chamber. During mixing, the vacuum pump reduces the pressure within the chamber to withdraw bubble gas from the cement and thereby reduce hollow inclusions in the cement when hardened.

After the cement has been properly mixed, the vacuum tube is removed from the mixing device, the pump is automatically turned off, the lid and mixer are removed and the mixed cement is promptly applied to the application site. The stem of a prosthetic element is then embedded into the cement. The cement hardens to form a strong joint securing the stem to the surrounding live bone.

Other objects and features of the invention will become apparent as the description proceeds, especially when taken in conjunction with the accompanying drawings illustrating the invention, of which there are two sheets and three embodiments.

DESCRIPTION OF THE PREFERRED EMBODIMENTS

Figure 1:
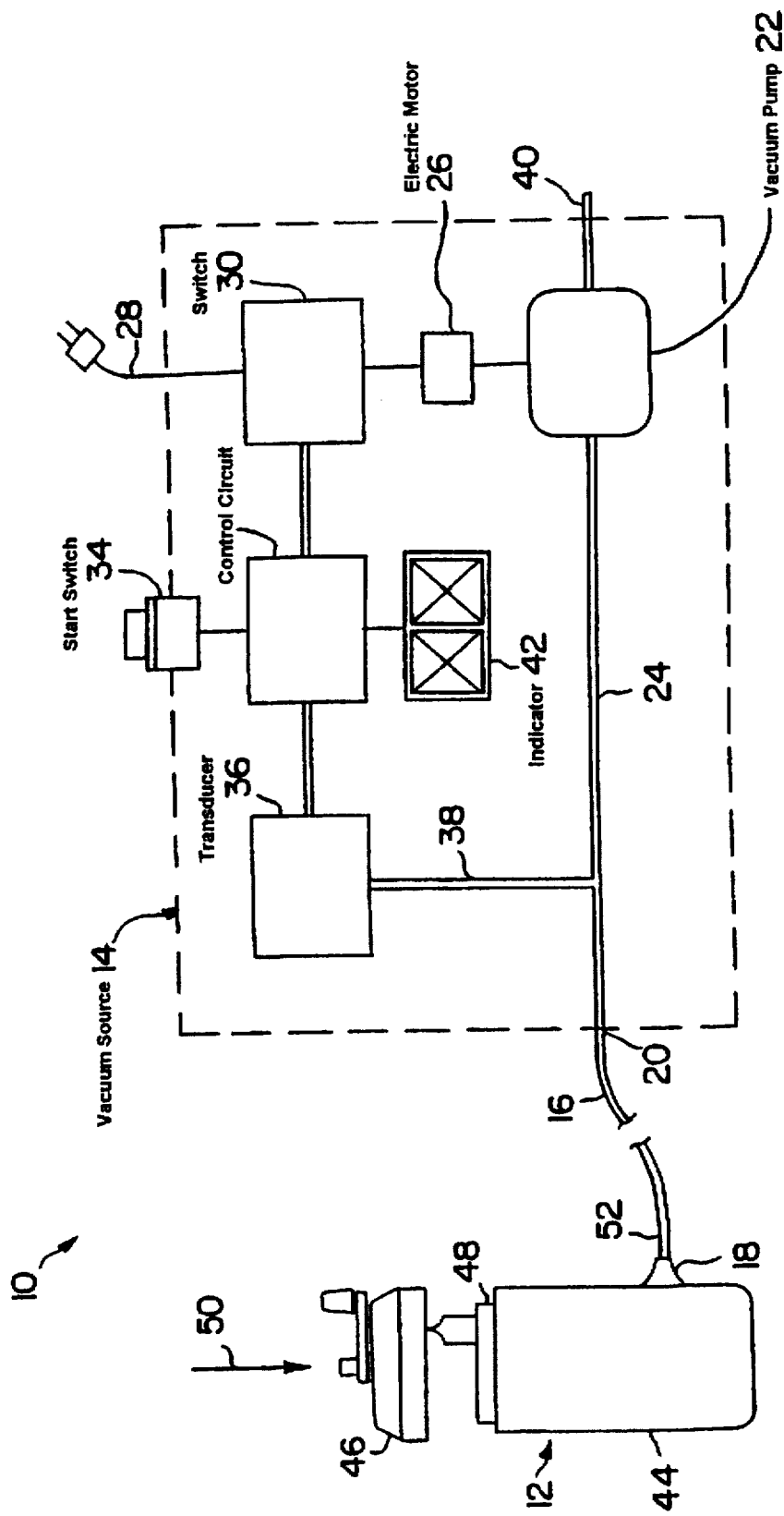
FIG. 1 illustrates the first embodiment bone cement mixing system.

The disclosure of U.S. Pat. No. 5,395,167 is incorporated herein by reference.

Bone cement mixing system 10 includes a bone cement mixer 12, and vacuum source 14. The mixer may be either an in-bowl mixer or an in-syringe mixer. Source 14 is illustrated diagrammatically. A vacuum tube 16 extends from a vacuum port 18 on the mixer to a low pressure inlet port 20 on vacuum source 14.

Source 14 includes a vacuum pump 22 having an inlet port connected to low pressure line 24 which extends to port 20. Pump 22 is driven by electric motor 26, which is connected to an electric power source through power line 28. Normally open control switch 30 is located in line 28. The switch is closed by a conventional control circuit 32. A manually actuated momentary start up switch 34 actuates the control to close switch 30 and actuate pump 22 in order to test operation of the vacuum system.

Electronic transducer control circuit 36, which may be of the type manufactured by Motorola, Inc. of Schaumburg, Ill., is connected to low pressure vacuum line 24 by vacuum line 38. The control circuit 36 actuates circuit 32 to close switch 30 and actuate vacuum pump 22 in response to a positive pressure pulse in low pressure line 24. Additionally, when the vacuum pump is operating to reduce the pressure in the mixer or maintain a low pressure in the mixer, the transducer 36 senses a sudden positive pressure pulse or increase in pressure in low pressure line 24 and actuates control circuit 32 to open switch 30 and turn off or deactivate the vacuum pump 24. The transducer distinguishes between a positive pressure pulse above ambient pressure, which turns the pump on, and a positive pressure pulse above a low pressure vacuum, which turns the pump off.

The vacuum source 14 includes a visible vacuum indicator 42, controlled by circuit 32, to provide a visual indication of the level of vacuum in the interior of the mixer 12 during mixing. Bone cement mixer 12 includes a cylindrical body 44 and a lid 46 which is fitted on the top of the body by sliding the lid down along top collar 48.

The bone cement mixing system is used during the mixing of bone cement in the operating room in order to remove air from the interior of the closed mixer during mixing. PMMA, and MMA, in proper proportions, are placed in the mixer body 14. The PMMA and MMA may be confined in a cartridge held in body 44, as disclosed in U.S. Pat. No. 5,395,167. Alternatively, the ingredients may be placed directly in the body of the mixer. In the letter case, port 18 would be located above the bone cement.

With the cement ingredients placed in the mixer and with the end of tube 16 mounted on vacuum port 18, lid 46 is moved down onto the mixer body in the direction of arrow 50 to close the interior of the mixer prior to mixing. Movement of the lid onto the body generates a positive pressure pulse in the interior of the mixer which is communicated along tube 16 and vacuum lines 16, 24 and 38 to the electronic transducer 36 in vacuum source 14. The transducer senses the pressure pulse and automatically and immediately turns on the vacuum pump 22, without the necessity of manual intervention. Operation of the vacuum pump withdraws air from the interior of the mixer during mixing. Mixing is conventionally performed by the operator manually rotating a mixing handle on the mixer.

During mixing, the pump withdraws air from the interior of the mixer to reduce or eliminate air bubbles from the interior of the mixed bone cement, as described in U.S. Pat. No. 5,395,167.

Mixed bone cement sets rapidly. For this reason, it is important that the mixed bone cement is promptly flowed to the application site after mixing has been completed. This is easily done by completing mixing, removing the end 52 of vacuum tube 16 from the vacuum port 18 to allow air to flow into the interior of the mixer and release lid 46 for easy manual removal from the top of body 44. Removal of tube 16 from the port generates a positive pressure pulse in the vacuum in tube 16, line 24 and line 38. This positive vacuum pulse is sensed by transducer 36 which actuates control circuit 32 to open switch 30 to shut down the vacuum pump, as described in further detail in U.S. Pat. No. 5,395,167.

In some bone cement mixers, it may be possible for an operator to remove the lid from the evacuated, low pressure mixer after mixing without prior removal of the tube from the mixer, and in that way generate a positive vacuum pulse for automatically shutting down the vacuum pump.

Figure 2:
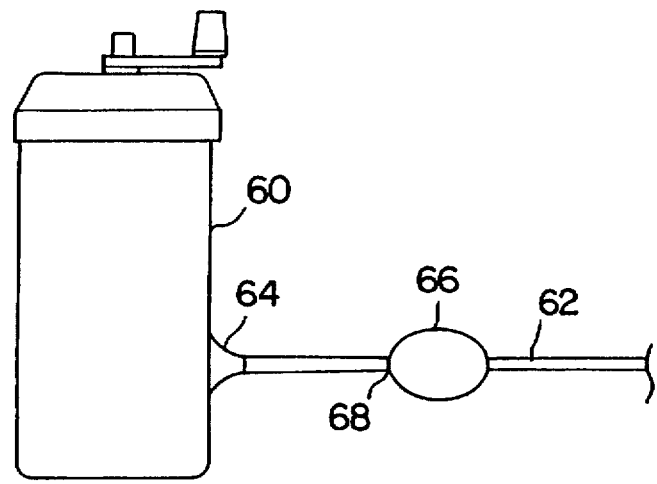
FIG. 2 illustrates part of the second embodiment bone cement mixing system.

FIG. 2 illustrates the second embodiment of the invention in which a bone cement mixer 60, like mixer 12, is connected to a vacuum source identical to source 14 (not illustrated) through a low pressure tube 62 having an end mounted on mixer vacuum port 64. A manually actuated squeeze or pressure bulb 66 is mounted in the tube 62 adjacent to mixer 60 and may include a one way check valve (not illustrated) in the end 68 of the bulb adjacent to the mixer. The check valve permits gas to flow along the tube toward the vacuum source; but prevents reverse flow.

The second embodiment bone cement mixing system is used as previously described except that after the bone cement ingredients to be mixed have been placed in the mixer the lid is placed on the top of the mixer body. This is done without generating a positive above-ambient pressure pulse sufficient to actuate the vacuum source. After the mixer has been closed and before mixing is initiated, the operator sharply squeezes bulb 66 to form a positive above ambient pressure pulse which flows along tube 62 and to the electronic transducer in the vacuum source to turn on the vacuum pump 22 automatically, as previously described. The check valve, if provided, at end 68 of the squeeze bulb prevents the pressure pulse from being dissipated by flowing into the interior of mixer 60 while permitting the vacuum pump to draw air from the mixer. After mixing has been completed, the operator removes the end of tube 62 from port 64 to deactivate the vacuum automatically pump, as previously described.

Figure 3:
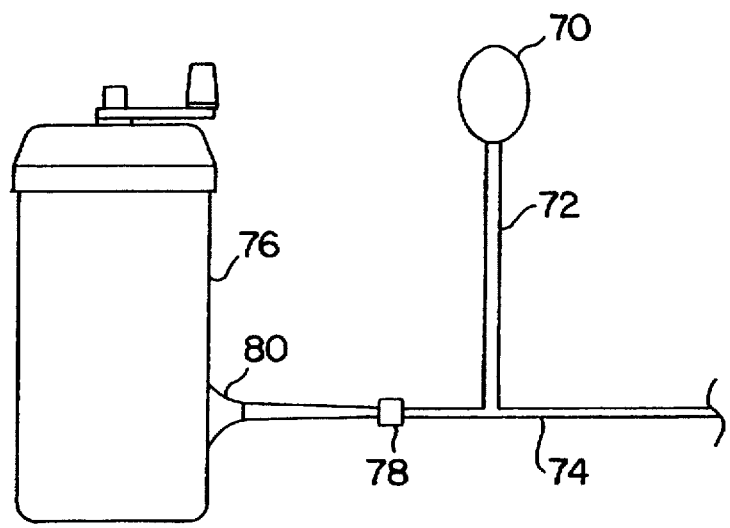
FIG. 3 illustrates part of the third embodiment bone cement mixing system.

FIG. 3 illustrates a third embodiment of the invention similar to the second embodiment, but in which manual squeeze or pressure bulb 70 is mounted on the end of a lateral vacuum tube 72 joining the main vacuum tube 74 extending between mixer 76 and a vacuum source (not illustrated) like source 14. After the bone cement ingredients have been placed in the mixer and the cap has been placed on the top of the mixer, bulb 70 is squeezed sharply to generate a positive above-ambient pressure pulse which is sensed by the vacuum source, as previously described, to actuate the vacuum pump and initiate evacuation of the mixer. A check valve 78 may be provided in tube 74 between the bulb and port 80 to prevent dissipation of the pulse, as described previously.

Both the second and third embodiment bone cement mixing systems use a manual squeeze or pressure bulb for automatically turning on the vacuum pump, in response to simple squeezing of the bulb. In both cases, the bulb may be positioned in a location convenient to the operator so that it is readily found and can be immediately actuated after closing of the bone cement mixer to save time and facilitate efficient mixing.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A system for mixing bone cement comprising.
   a) a device for mixing bone cement having a hollow mixing chamber and a vacuum port;
   b) a vacuum tube having a first end attached to said port and a second end; and
   c) a vacuum source including a vacuum pump having an inlet port connected to the second end of the vacuum tube, and a vacuum pump start and stop device operatively joined to the pump to start the pump in response to a positive pressure pulse above ambient and to automatically stop the pump in response to a positive pressure pulse above a vacuum.

2. A system as in claim 1 including an electric motor for the pump, a power line for the motor and wherein the vacuum pump start and stop device includes an electronic pressure transducer connected to the inlet port, a power switch connected in the power line for the motor and a circuit element operable to actuate the switch when the transducer senses a positive pressure pulse at the inlet port.

3. A system as in claim 2 including a piston lid for the hollow mixing chamber whereby closing the lid onto the chamber causes an increase in pressure.

4. A system as in claim 2 including a pressure bulb connected to the vacuum tube whereby squeezing the bulb causes an increase in pressure.

5. A system as in claim 4 including a check valve between the bulb and the mixing chamber.

6. A system as in claim 2 including a second tube joining the vacuum tube and a pressure bulb on the end of the second tube.

7. A system for mixing bone cement including a bone cement mixing chamber, a vacuum source, a first tube joining the vacuum source to the interior of the mixing chamber so that the source reduces the pressure within the chamber, a pressure pulse generator connected to either the mixing chamber or the first tube, and a sensing circuit operably connected to the vacuum source to actuate the vacuum source in response to a pressure pulse from said pulse generator.

8. A system as in claim 7 wherein said pulse generator compresses a squeeze bulb connected to said tube.

9. The device of claim 7 wherein said pulse generator includes a piston lid for the mixing chamber.

10. The device of claim 7 wherein said pulse generator includes a bulb joined to the vacuum tube whereby squeezing the bulb causes a pressure pulse to activate the vacuum source.

11. A device as in claim 10 including a check valve located between the bulb and the chamber.

12. The device of claim 7 wherein said pulse generator includes a squeeze bulb and a second tube extending between the first tube and the bulb.

13. A device as in claim 12 including a check valve in the first tube adjacent the mixing chamber.

* * * * *

UNITED STATES PATENT AND TRADEMARK OFFICE
CERTIFICATE OF CORRECTION

PATENT NO. : 5,797,680
DATED : August 25, 1998
INVENTOR(S) : William M. Murray

It is certified that error appears in the above-identified patent and that said Letters Patent is hereby corrected as shown below:

In the Title Page:
    In the illustrative figure, a reference number 32 should be applied to the box labeled "Control Circuit".
In the Specification:
    Column 3 line 30, following "body", change "14" to --44--.
In the Drawings:
    Sheet 1, Figure 1, a reference numeral 32 should be applied to the box labeled "Control Circuit".

Signed and Sealed this

Ninth Day of March, 1999

Attest:

Q. TODD DICKINSON

*Attesting Officer*     Acting Commissioner of Patents and Trademarks